US012128342B2

(12) United States Patent
Dundek et al.

(10) Patent No.: US 12,128,342 B2
(45) Date of Patent: Oct. 29, 2024

(54) GAS FILTER HOUSING WITH REPLACEABLE GAS FILTER MEDIA FOR MEDICAL VENTILATION SYSTEMS

(71) Applicant: Vayu Global Health Innovations, LLC, Medford, MA (US)

(72) Inventors: Michelle Dundek, Medford, MA (US); Akash Premkumar, Medford, MA (US); Ellie Ng, Medford, MA (US); Thomas Burke, Medford, MA (US)

(73) Assignee: Vayu Global Health Innovations, Public Benefit Corporation, Medford, MA (US)

( * ) Notice: Subject to any disclaimer, the term of this patent is extended or adjusted under 35 U.S.C. 154(b) by 558 days.

(21) Appl. No.: 17/444,797

(22) Filed: Aug. 10, 2021

(65) Prior Publication Data

US 2022/0040618 A1   Feb. 10, 2022

Related U.S. Application Data

(60) Provisional application No. 63/063,693, filed on Aug. 10, 2020.

(51) Int. Cl.
*B01D 46/00*   (2022.01)
*A61M 16/08*   (2006.01)
(Continued)

(52) U.S. Cl.
CPC ....... *B01D 46/0005* (2013.01); *A61M 16/085* (2014.02); *A61M 16/105* (2013.01);
(Continued)

(58) Field of Classification Search
CPC ...... A61M 16/105–107; A61M 16/085; B01D 46/0012; B01D 46/0005; B01D 46/10;
(Continued)

(56) References Cited

U.S. PATENT DOCUMENTS 3,512,648 A    5/1970   Bittner et al.
3,841,145 A *  10/1974  Boubel ................ B01D 46/442
                                                       73/863.25
(Continued)

FOREIGN PATENT DOCUMENTS

DE    19615290 A1    1/1998
WO     9748433 A1   12/1997
WO     9903525 A1    1/1999

OTHER PUBLICATIONS

Pari GMBH, Filter/Ventil Set, 2012, pp. 23-42, Germany.
(Continued)

*Primary Examiner* — Robert Clemente
(74) *Attorney, Agent, or Firm* — Intrinsic Law Corp.

(57) ABSTRACT

A medical breathing gas filter housing includes a first housing body including a first port, and a second housing body including a second port. The gas filter housing is configurable between a closed state and an open state. In the closed state, the first housing body is snap fit to the second housing body such that first and second interior sides of the first and second housing bodies, respectively, define a cavity, the cavity sized to receive a replaceable gas filter media. In the open state, the first housing body is separated from the second housing body to provide access to the cavity.

23 Claims, 16 Drawing Sheets

(51) Int. Cl.
    *A61M 16/10* (2006.01)
    *B01D 46/42* (2006.01)

(52) U.S. Cl.
    CPC ......... *B01D 46/0012* (2013.01); *B01D 46/42* (2013.01); *B01D 2265/028* (2013.01); *B01D 2265/029* (2013.01); *B01D 2271/027* (2013.01)

(58) Field of Classification Search
    CPC ........ B01D 2265/028; B01D 2271/027; B01D 46/42; B01D 2265/029
    See application file for complete search history.

(56) References Cited

U.S. PATENT DOCUMENTS

| | | | | |
|---|---|---|---|---|
| 4,128,407 A | * | 12/1978 | Chapel | A61M 16/1055 |
| | | | | 210/501 |
| 4,911,840 A | | 3/1990 | Underwood | |
| 5,337,739 A | | 8/1994 | Lehman | |
| 5,390,668 A | * | 2/1995 | Lehman | B01D 46/0028 |
| | | | | 96/108 |
| 5,592,933 A | * | 1/1997 | Zucchi | B01D 46/64 |
| | | | | 128/205.27 |
| 6,033,455 A | * | 3/2000 | Kurashima | B01D 46/0015 |
| | | | | 55/497 |
| 6,833,023 B1 | | 12/2004 | Vandenberghe et al. | |
| 7,993,071 B2 | | 8/2011 | Clawson | |
| 2004/0211161 A1 | | 10/2004 | Avery | |
| 2008/0028734 A1 | * | 2/2008 | McClain | B01D 46/0012 |
| | | | | 55/505 |
| 2008/0157420 A1 | | 7/2008 | Mayer | |
| 2018/0333555 A1 | | 11/2018 | Burke et al. | |

OTHER PUBLICATIONS

D. Cramter et al., "Bacterial/Viral Filters in Pulmonary Function Departments", The Buyers' Guide to Respiratory Care Products, 2007, pp. 149, United Kingdom.

ISR, "International Search Report", PCT/US2021/071149, Oct. 29, 2021.

European Patent Office, extended European Search Report for EP Application No. 21856886.3 dated Jul. 7, 2024.

Canadian Intellectual Property Office, Office Action for CA Application No. 3,186,890 dated Jul. 31, 2024.

* cited by examiner

GAS FILTER HOUSING WITH REPLACEABLE GAS FILTER MEDIA FOR MEDICAL VENTILATION SYSTEMS

CROSS-REFERENCE TO RELATED APPLICATIONS

This application claims priority to U.S. Provisional Application No. 63/063,693, titled "Replaceable Gas filter housing for Medical Ventilation Systems," filed on Aug. 10, 2020, which is hereby incorporated by reference.

TECHNICAL FIELD

This application relates generally to gas filters for medical ventilation systems.

BACKGROUND

Medical breathing systems such as mechanical ventilators, Continuous Positive Airway Pressure (CPAP) systems, oxygen delivery systems, etc. deliver breathing gases to patients and/or remove excess and exhaled gases.

CPAP systems are effective at providing non-invasive ventilation often supplemented with additional oxygen for newborns with respiratory distress, over one million of whom die each year before 28 days of life. In a hospital setting, it is possible to connect tubes from a tank of air and a tank of oxygen to provide a mixture of air and oxygen, which is generally necessary since 100% oxygen is associated with damage to the eye, brain, and other organs. A pulse oximeter is used to monitor the blood oxygen concentration of the patient. In hospital settings especially in high-resource areas, CPAP systems require electric power, either via connection to an electric wall socket or to a battery, to control the heat, humidification, and oxygen concentration of oxygen-enriched air to the patient. Such systems are expensive and difficult to transport due to the weight of the air tank, oxygen tank, the pump-based CPAP with pressure control, and accessories. Furthermore, there is a need for electric power to operate these systems.

In bubble CPAPs (bCPAPs), the positive airway pressure is provided by breathing into a bottle containing water (bubbler) with the tube containing the expired air maintained at a known depth in the water. The water-depth of the exiting expired air from the patient controls the amount of back pressure to assist in ventilation at the alveolar level. An advantage of some bCPAPs is they do not use an air tank or electricity to produce a blend of air and oxygen to the patient, but instead use ambient air, which enters the oxygen stream through air entrainment ports of a device referred to as an ambient air-oxygen blender.

Air exhaled by patients on CPAP and bCPAP systems is emitted into the patients' rooms. This may increase the risk of infection to hospital staff, visitors, and other patients due to pathogens that may be present in the consumed air. For example, in the 2020 global pandemic for the COVID-19 virus, it is desirable to reduce and/or eliminate airborne particulates, aerosols, droplets, and/or other particles in the consumed air that may be contaminated with the COVID-19 virus.

This is one reason these systems often require bacterial viral filters to filter the inspiratory and/or expiratory gases. These filters can perform a variety of roles, including but not limited to: filtering breathing gases from non-medical grade sources, such as air sourced from the ambient environment, before they reach the patient; filtering the exhaled gases of the patient before they are exhausted into the room, to protect others being exposed to any pathogens in the exhaled gases; and/or connecting to the inlet of a machine, such as a ventilator, to prevent contamination of the reusable components of the machine from the patient's exhaled gases.

These filters are disposable, and typically last 24-48 hours. As multiple filters may be used simultaneously for one patient, who could be getting treatment for an extended time, the disposable nature of these filters creates a lot of waste. Additionally, the bulky shape means these filters take up a large amount of space, which makes them difficult to store and expensive to ship.

During the 2020 global pandemic for the COVID-19 virus, as demand for ventilators has expanded, so has demand for the consumables needed to support a patient on a ventilator, including bacterial viral filters. This has created a shortage of these filters, which has been exacerbated by the limitations described above.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a gas filter housing comprising: a first housing body including a first port; and a second housing body including a second port. The gas filter housing is configurable between a closed state and an open state. In the closed state, the first housing body is snap fit to the second housing body such that first and second interior sides of the first and second housing bodies, respectively, define a cavity, the cavity sized to receive a replaceable gas filter media. In the open state, the first housing body is separated from the second housing body to provide access to the cavity.

In one or more embodiments, a gasket disposed on or in the first housing body, wherein in the closed state the gasket is disposed at an interface between the first and second housing bodies to improve a fluid seal therebetween. In one or more embodiments, the first housing body includes a first flange, the second housing body includes a second flange, and in the closed state, the first flange is disposed on the second flange. In one or more embodiments, a plurality of snap clips is attached to the first housing body, the snaps clips configured to releasably engage the second housing body. In one or more embodiments, each snap clip includes a respective hook configured to releasably engage the second flange. In one or more embodiments, a first ridge extends from the first interior side of the first housing body, a second ridge extends from the second interior side of the second housing body, and when the gas filter housing is in the closed state, the first and second ridges engage top and bottom sides, respectively, of the replaceable gas filter media.

Another aspect of the invention is directed to a gas filter housing comprising: a first housing body comprising a first conical body, a first tubular body, and a first flange, the first conical body tapering from a first end to a second end, the first tubular body attached to the second end of the first conical body to form a first port, the first flange disposed at the first end of the first conical body; a second housing body comprising a second conical body, a second tubular body, and a second flange, the second conical body tapering from a first end to a second end, the second tubular body attached to the second end of the second conical body to form a second port, the second flange coupled to the second end of the second conical body; and a plurality of snap clips. Each snap clip comprises: a rigid projection having opposing planar surfaces, the rigid projection extending from the first flange; a hook attached to an end of the rigid projection; and a slot defined in the second flange, the slot configured to removably receive the hook and the rigid projection. The gas filter housing is configurable between a closed state and an open state. In the closed state: the first flange is disposed on the second flange such that first and second interior sides of the first and second housing bodies, respectively, define a cavity, the cavity sized to receive a replaceable gas filter media, and in each snap clip, the hook and the rigid projection are inserted through the slot and the hook engages the second flange to secure the snap clip. In the open state: in each snap clip, the hook is disengaged from the second flange and the hook and the rigid projection are removed from the slot, and the first flange is spaced apart from the second flange to provide access to the replaceable gas filter media.

In one or more embodiments, a first ridge extends from the first interior side of the first housing body, a second ridge extends from the second interior side of the second housing body, and when the gas filter housing is in the closed state, the first and second ridges engage top and bottom sides, respectively of the replaceable gas filter media. In one or more embodiments, the first and second ridges are aligned when the gas filter housing is in the closed state.

In one or more embodiments, the first and second ridges are first and second inner ridges, respectively, an outer ridge extends from the first interior side of the first housing body, a groove is defined in the second interior side of the second housing body, and when the gas filter housing is in the closed state, the outer ridge is disposed in the groove. In one or more embodiments, when the gas filter housing is in the closed state, the outer ridge and the groove form a seal.

In one or more embodiments, the outer ridge is a first outer ridge, a second outer ridge extends from the second interior side of the second housing body, and the groove is defined between the second outer ridge and the second flange. In one or more embodiments, a sealing outer ridge extends from the first interior side of the first housing body, a sealing channel is defined between the sealing outer ridge and the first outer ridge, and a gasket is disposed in the sealing channel. In one or more embodiments, the gasket comprises an O-ring. In one or more embodiments, the second housing body further comprises an annular body, the annular body disposed between the second conical body and the second flange, the annular body further defining the sealing channel.

In one or more embodiments, the filter housing further comprises a hinge attached to the first and second housing bodies. In one or more embodiments, the first and second ports are aligned along an axis of symmetry of the filter housing.

Another aspect of the invention is directed to a gas filter housing comprising: a first housing body comprising a first conical body, a first tubular body, and a first flange, the first conical body tapering from a first end to a second end, the first tubular body attached to the second end of the first conical body to form a first port, the first flange disposed at the first end of the first conical body; and a second housing body comprising a second conical body, a second tubular body, an annular body, and a second flange, the second conical body tapering from a first end to a second end, the second tubular body attached to the second end of the second conical body to form a second port, the annular body disposed between the second conical body and the second flange. The gas filter housing is configurable between a closed state and an open state. A plurality of ridges, including a pair of neighboring ridges, are attached to a first interior side of the first tubular body. The first and second housing bodies include complementary threaded surfaces. In the closed state: the first flange is disposed on the second flange such that first and second interior sides of the first and second housing bodies, respectively, define a cavity, the cavity sized to receive a replaceable gas filter media, and the complementary threaded surfaces that are rotatably engaged to secure the gas filter housing. In the open state: the first flange is spaced apart from the second flange to provide access to the replaceable gas filter media, and the complementary threaded surfaces on the first and second housing bodies are disengaged.

In one or more embodiments, in the closed state the pair of neighboring ridges extend to the annular body. In one or more embodiments, the gas filter housing further comprises a gasket disposed in a sealing channel defined between the pair of neighboring ridges, the sealing channel further defined by the annular body. In one or more embodiments, the gasket comprises an O-ring.

In one or more embodiments, the gas filter housing further comprises a sampling port disposed on the first exterior side of the first housing body, the sampling port fluidly coupled to the cavity when the gas filter housing is in the closed state. In one or more embodiments, the first and second ports are aligned along an axis of symmetry of the filter housing.

BRIEF DESCRIPTION OF THE DRAWINGS

For a fuller understanding of the nature and advantages of the concepts disclosed herein, reference is made to the detailed description of preferred embodiments and the accompanying drawings.

DETAILED DESCRIPTION

This application discloses a housing for replaceable/disposable filter media for medical ventilation and oxygen delivery systems (e.g., CPAP or bCPAP) that can be used to reduce and/or eliminate airborne particulates, aerosols, droplets, and/or other particles in inhaled and/or exhaled air that may be contaminated with pathogens such as the COVID-19 virus in the 2020 global pandemic.

Figure 1:
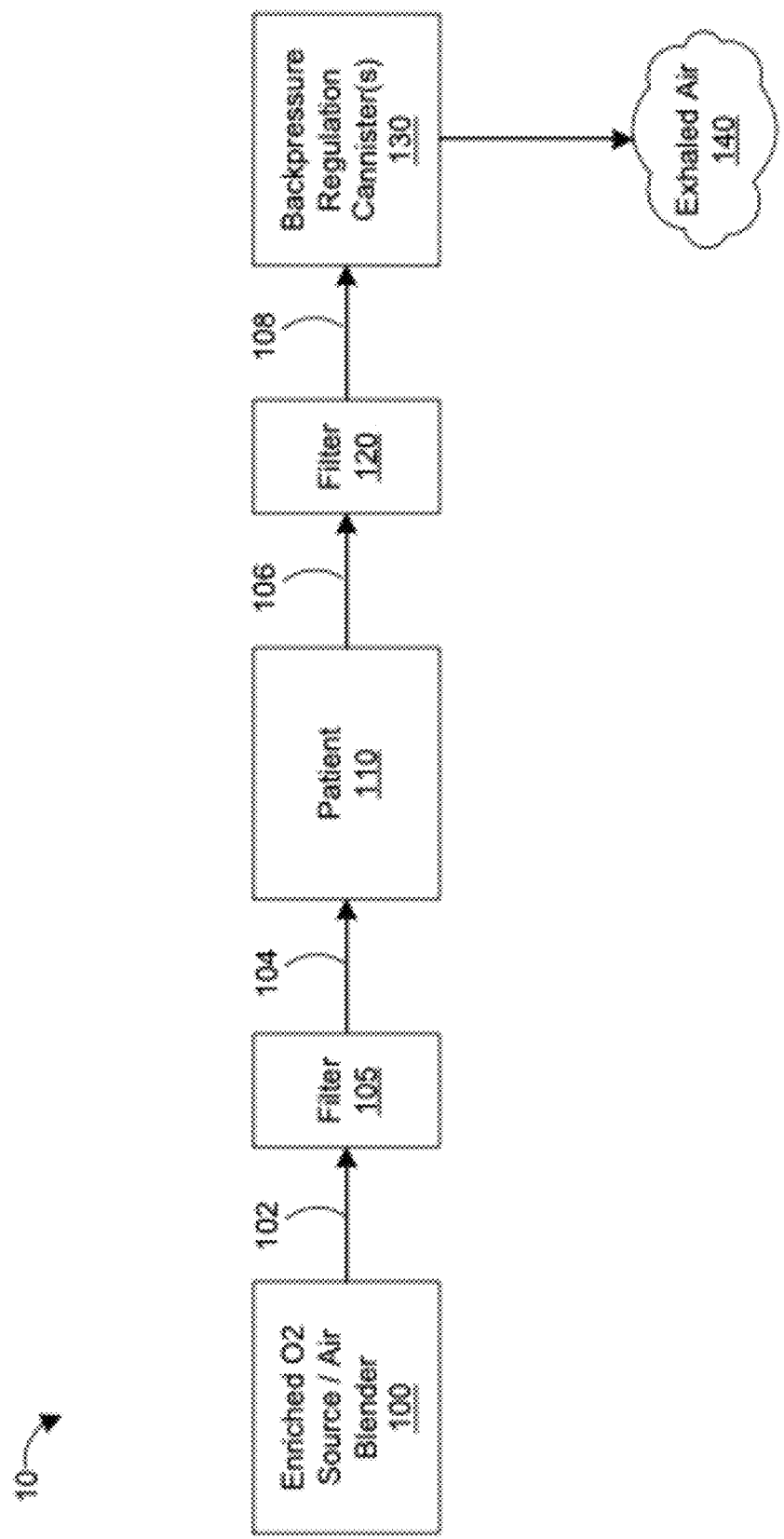
FIG. 1 is a schematic block diagram of a bCPAP system according to an embodiment.

FIG. 1 is a schematic block diagram of a bCPAP system 10 according to an embodiment. The system 10 includes an oxygen-enriched air source 100, filters 105 and 120, and backpressure cannister(s) 130. The air source 100 is configured to provide oxygen-enriched air to a patient 110 to assist in breathing, for example during respiratory distress. The oxygen-enriched air source 100 can comprise tanks of oxygen and medical air or an air blender that mixes ambient air with an oxygen source. An example of an air blender is disclosed in U.S. Patent Application Publication No. 2018/0333555, titled "Adjustable Ambient Air-Oxygen Blender," which is hereby incorporated by reference. The oxygen-enriched air source 100 can be regulated in terms of flow rate, pressure, temperature, and/or humidity.

The oxygen-enriched air flows through an optional supply tube 102 to a first filter 105 and then through a supply tube 104 that extends from the first filter 105 to the patient 110. The patient 110 may use a breathing apparatus, such as a nasal tube, nasal mask, or face mask, to receive (e.g., breathe in) the oxygen-enriched air. The consumed air is exhaled through a first exhalation tube 106 that extends from the patient 110 (e.g., the breathing apparatus) to a second filter 120 and an outlet tube 108 that extends from the second filter 120 to the backpressure regulation cannister 130.

The backpressure regulation cannister 130 is filled with water to provide hydrostatic backpressure. The distal end of the outlet tubing 108 is submerged in the water so that gas is forced to exit the system by pressing against the column of water in the submerged tubing, and the entire system is pressurized to a constant level equivalent to the depth of submersion of the tubing in the water. The gas passes through the water as gas bubbles into the environment.

The filters 105 and 120 can comprise N95 filter media (e.g., that meets the N95 classification by the U.S. National Institute for Occupational Safety and Health) or a higher-rating filter media (e.g., N100) that can reduce and/or eliminate airborne particulates, aerosols, droplets, and/or other particles in the inhaled and exhaled air that may be contaminated with a pathogen, such as the COVID-19 virus in the 2020 global pandemic. The filters 105 and 120 also comprise a housing that surrounds the filter media and connects in-line with tubing such as 102 and 104, and 106 and 108, respectively, to direct air flow through the filter media. The oxygen-enriched air is initially filtered by filter 105, delivered to the patient, and then the consumed air is filtered again (by filter 120) and released into the environment (e.g., patient's room) as exhaled air 140.

The following describes example embodiments of a gas filter housing which can be assembled with a replaceable gas filter media to function as filter 105 and/or 120.

Figure 2:
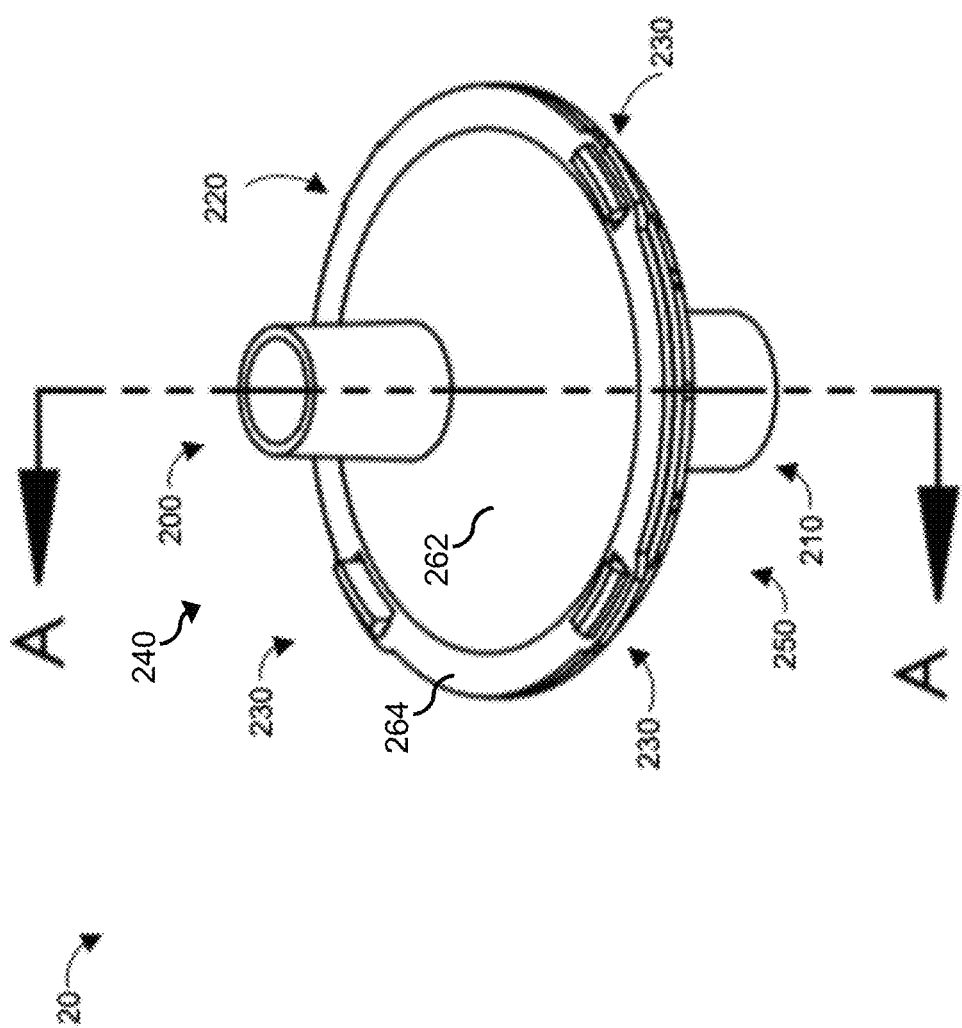
FIG. 2 is a perspective view of a gas filter housing in a closed state according to an embodiment.

FIG. 2 is a perspective view of a medical breathing gas filter housing 20 in a closed state according to an embodiment. The gas filter housing 20 includes ports 200 and 210 that are configured to be releasably attached to tubes (e.g., inhalation tubes or exhalation tubes) in a mechanical ventilation system such as bCPAP system 10 or another CPAP system. Consumed air from the patient flows through the exhalation tube into an inlet port 200 where it then flows through a replaceable gas filter media (such as the gas filter media in filter 105 or 120) disposed in a cavity defined in the gas filter housing 20. The filtered air then flows through an outlet port 210 into another tube. The outlet tube can be connected to another component of the mechanical ventilation system such as a backpressure regulation cannister (e.g., backpressure regulation cannister(s) 130). Alternatively, the filtered consumed air can flow out of the outlet port 210 directly into the room.

Ports 200, 210 can include standardized connectors that allow the ports 200, 210 to be releasably connected and/or releasably attached to standard-sized tubes and/or other components. For example, the ports 200, 210 can include ISO 15F (e.g., 15 mm female) and 15M (e.g., 15 mm male) connectors, respectively. Alternatively, the ports 200, 210 can include double-wall connectors that have two different standard-sized connectors such as ISO 15F/22M (e.g., 15 mm female and 22 mm male) and ISO 15M/22F (e.g., 15 mm male and 22 mm female) connectors, respectively. Other sized connectors, such as custom-sized, non-standard-sized, or other standard sized connectors can be used in ports 200, 210. Either port 200, 210 can function as an inlet port or as an outlet port. When one port 200, 210 is the inlet port, the other port 210, 200, respectively, is the outlet port.

The replaceable gas filter media can include an N95 filter media or higher (e.g., surgical N95, N100, or other filter) that may be effective in reducing and/or filtering out airborne particulates, aerosols, droplets, and/or other particles in the consumed air that may be contaminated with a pathogen (e.g., virus and/or bacteria), such as the COVID-19 virus in the 2020 global pandemic. The filter media can be disposable and/or single-use to reduce cross-contamination between patients.

The gas filter housing 20 includes top and bottom housing bodies 240, 250, respectively, that are pivotably connected by a hinge 220 or other mechanical attachment means. In the closed state, the top and bottom housing bodies 240, 250 are releasably secured (e.g., snap fit) by snap clips 230 that are attached to the top and bottom housing bodies 240, 250. The top and bottom housing bodies 240, 250 are symmetrical and/or complementary such that when the top and bottom housing bodies 240, 250 are secured by the snap clips 230, a gas seal is formed. In some embodiments, a gasket such an O-ring can be disposed between the top and bottom housing bodies 240, 250 (e.g., at or between an interface between the top and bottom housing bodies 240, 250) to provide and/or improve the gas seal when the gas filter housing 20 is in the closed state.

Figure 4:
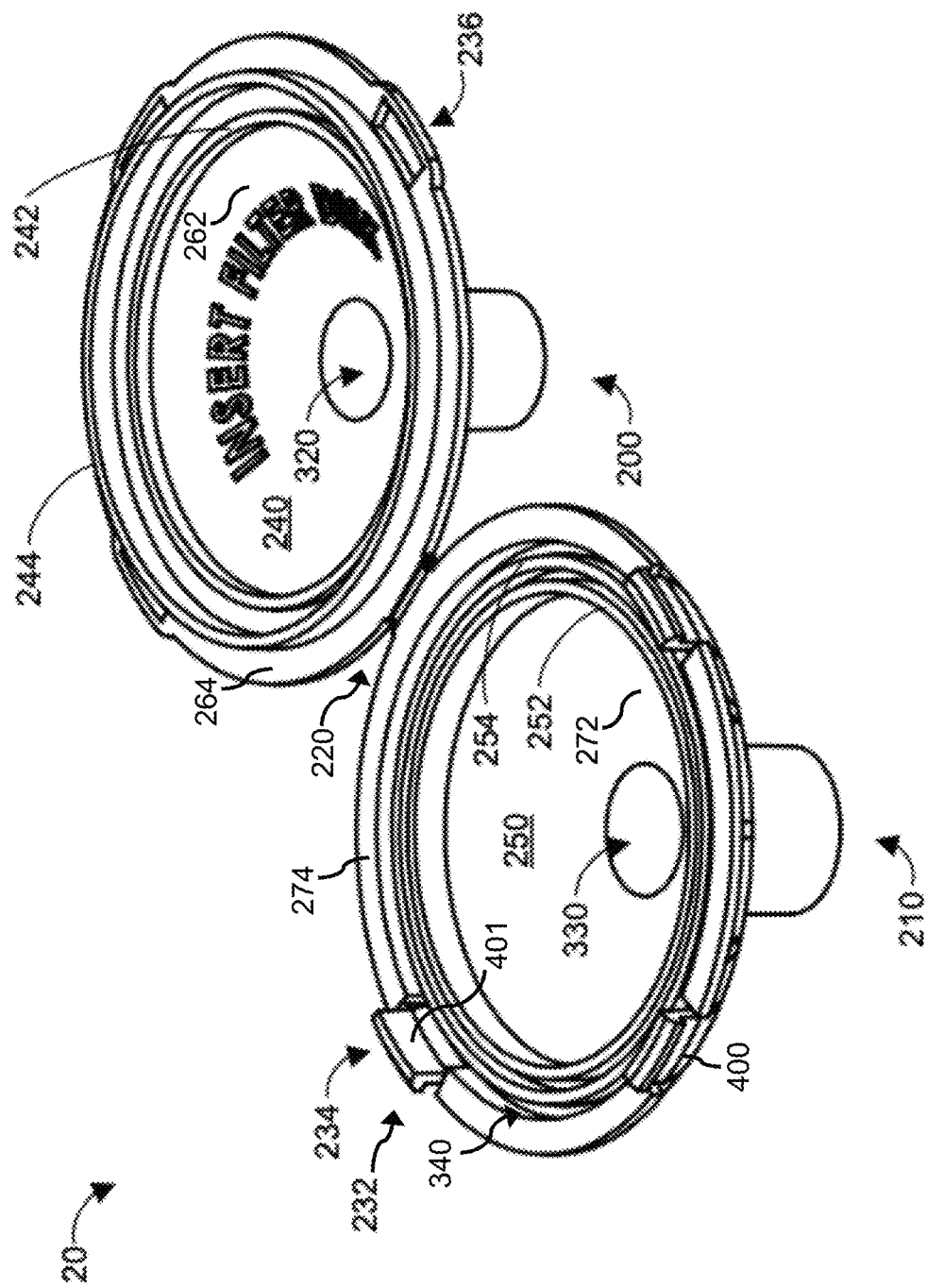
FIG. 4 is a perspective view of the gas filter housing illustrated in FIG. 2 in an open state with the gas filter media removed.

The top housing body 240 includes a conical portion 262 and a flange 264. The conical portion 262 is disposed between and/or is attached to the inlet port 200 and the flange 264. The snap clips 230 and the hinge 220 are partially or fully attached to the flanges 264, 274, as illustrated in FIG. 4.

Figure 3:
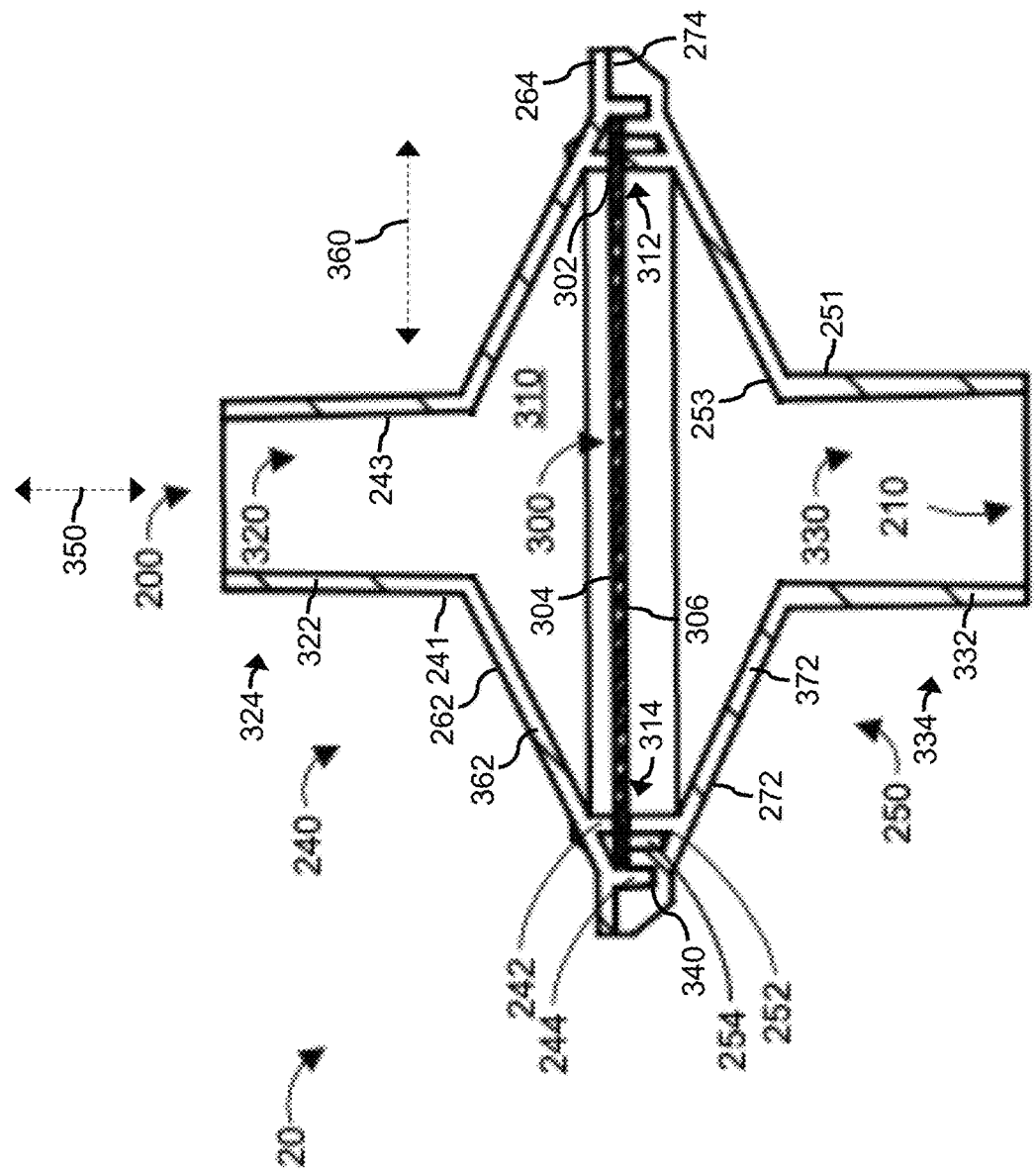
FIG. 3 is a cross-sectional view of the gas filter housing illustrated in FIG. 2.

FIG. 3 is a cross-sectional view of gas filter housing 20 through line A-A in FIG. 2. As illustrated, the bottom housing body 250 includes a conical portion 272 and a flange 274. The conical portions 262, 272 are formed by walls 362, 372, and the walls 362, 372 define a cavity 310. The cavity 310 is configured and/or sized to receive a replaceable gas filter media 300 such that the replaceable gas filter media 300 extends from a first end 312 to a second end 314 of the cavity 310. The top and bottom housing bodies 240, 250 have a respective exterior side 241, 251 and a respective interior side 243, 253.

A first channel 320 extends between and fluidly couples the first port 200 and the cavity 310. A second channel 330 extends between and fluidly couples the second port 210 and the cavity 310. The ports 200, 210 are aligned along a vertical axis of symmetry 350 through the gas filter housing 20. The vertical axis of symmetry 350 is orthogonal to the top and bottom surfaces 304, 306 of the replaceable gas filter media 300. When the first port 200 is the inlet port and the second port 210 is the outlet port, the first channel 320 is an inlet channel and the second channel 330 is an outlet channel. Conversely, when the second port 210 is the inlet port and the first port 200 is the outlet port, the first channel 320 is the outlet channel and the second channel 330 is the inlet channel. The first and second channels 320, 330 are defined by walls 322, 332, respectively. The walls 322, 332 form tubular portions 324, 334, respectively.

The conical portions 262, 272 are oriented in opposing directions to form a complementary structure in which the top conical portion 262 is disposed on the bottom conical portion 272. The portion of the top conical portion 262 near the first channel 320 has a narrower cross-sectional width than the portion of the top conical portion 262 near the replaceable gas filter media 300. In addition, the portion of the bottom conical portion 272 near the second channel 330 has a narrower cross-sectional width than the portion of the bottom conical portion 272 near the replaceable gas filter media 300. The cross-sectional width of the conical portions 262, 272 can be measured with respect to a horizontal axis 360 that is parallel to the top and bottom surfaces 304, 306 of the replaceable gas filter media 300 and that is orthogonal to the vertical axis of symmetry 350.

The top and bottom housing bodies 240, 250 include first and second inner ridges 242, 252 that are aligned with one another. For example, the inner ridges 242, 252 are disposed at the same radius from the vertical axis of symmetry 350. The inner ridges 242, 252 are configured to grip, compress, and/or engage the top and bottom sides 304, 306 of the replaceable gas filter media 300 along its sides or edges 302 when the gas filter housing 20 is in the closed state. The inner ridges 242, 252 can extend in circles or rings along conical portions 262, 272, respectively, defined by their respective radii. The cross-sectional thickness of the second inner ridge 252 can be greater than (e.g., 2 or 3 times) the cross-sectional thickness of the first inner ridge 242. The cross-sectional thicknesses of the inner ridges 242, 252 can be measured with respect to the vertical axis of symmetry 350. The inner ridges 242, 252 can further define the cavity 310.

The top and bottom housing bodies 240, 250 also include first and second outer ridges 244, 254 that are configured to form an airtight seal at and/or along the edge of the conical portions 262, 272, respectively, when the gas filter housing 20 is in the closed state. The outer ridges 244, 254 are horizontally (e.g., radially) offset from each other and in direct physical contact with each other. For example, the outer ridges 244, 254 are disposed at the different radii from the vertical axis of symmetry 350. The first outer ridge 244 is disposed in a slot or groove 340 defined in the bottom housing body 250. The slot or groove 340 is defined between outer ridge 254 and flange 274 such that the first outer ridge 244 blocks or substantially blocks gas from flowing laterally out of the cavity 310. The inner ridges 242, 252 and the outer ridges 244, 254 are parallel or substantially parallel (e.g., within 5° or within 1°) with one another and with vertical axis of symmetry 350. The cross-sectional thickness of the first outer ridge 244 can be greater than or equal to the cross-sectional thickness of the second outer ridge 254. The cross-sectional thicknesses of the outer ridges 244, 254 can be measured with respect to the vertical axis of symmetry 350.

The ends of the second inner and outer ridges 252, 254 and the first inner ridge 242 can be in direct physical contact with the replaceable gas filter media 300. The inner side of the first outer ridge 244 can be in direct physical contact with the replaceable gas filter media 300.

FIG. 4 is a perspective view of gas filter housing 20 in an open state with the gas filter media 300 removed. As illustrated, the snap clips 230 are formed by a rigid projection 232 that extends vertically (e.g., orthogonally) from the flange 274 of the bottom housing body 250. The rigid projection 232 is configured to fit snugly within a corresponding slot 236 in the top housing body 240. The rigid projection 232 includes a body having opposing planar surfaces 400, 401. A hook 234 is disposed at the end of the rigid projection 232 (e.g., where the rigid projection 232 is disposed between the hook and the flange 274) to attach to an edge of the slot 236 (e.g., to flange 264) after the rigid housing body 232 is inserted through slot 236. The hook 234 extends orthogonally or substantially orthogonally from the planar surfaces 400, 401. Neighboring snaps clips 230 can be disposed about 90° from each other along the flange 274. The hinge 220 can be disposed about 90° from the neighboring snap clips 230.

The slots 236 are defined in the flange 264 of the top housing body 240. The flanges 264, 274 are in the shape of a ring or annulus and the slots 236 define an arc along flange 264. The body of each rigid projection 232 is in the shape of a complementary arc along flange 274.

In the illustrated embodiment, the hook 234 extends orthogonally or substantially orthogonally from the outer planar surface 400 in a direction away from the housing bodies 240, 250. In another embodiment, the hook can extend orthogonally or substantially orthogonally from the inner planar surface 401. Pressing inwardly on the rigid housing body 232 (e.g., towards the housing bodies 240, 250) can release the hook 234 from the slot 236. In an alternative embodiment, the rigid projection 232 of each snap clip 230 can be disposed on the top housing body 240 and the slot 236 can be formed in the bottom housing body 250. In yet another embodiment, some snap clips 230 can be configured with the rigid projection 232 on the bottom housing body 250 and the corresponding slot 236 in the top housing body 240, and some snap clips 230 can be configured with the rigid projection 232 on the top housing body 240 and the corresponding slot 236 in the bottom housing body 250.

In another embodiment, magnets can be used to releasably secure the top and bottom housing bodies 240, 250 together. The magnets can be used in addition to or in place of the snap clips 230. In one example, the magnets can be arranged on both the top and bottom housing bodies 240, 250 such that in the closed state the corresponding magnets on the top and bottom housing bodies 240, 250 are oriented to have opposite polarities facing each other (and thus are attracted to each other). Alternatively, magnets can be disposed on only one housing body (e.g., the top housing body 240) and a ferromagnetic material is disposed at a corresponding location on the other housing body (e.g., the bottom housing body 250) such that the magnets are attracted to the corresponding ferromagnetic materials. In another embodiment, magnets can be disposed on the top housing body 240 and ferromagnetic materials can be disposed on the bottom housing body 250 at locations that correspond to the magnets on the top housing body 240, and magnets can be disposed on the bottom housing body 250 and ferromagnetic materials can be disposed on the top housing body 240 at locations that correspond to the magnets on the bottom housing body 250.

It will be apparent to those of skill in the art that additional and/or alternative attachment techniques can be used to releasably secure the top and bottom housing bodies 240, 250 together. For example, a latch, one or more screws, one or more bolts, cable ties, a clamp, hook-and-loop fasteners, snaps, and/or another mechanical fastener can be used to releasably secure the top and bottom housing bodies 240, 250.

Figure 5:
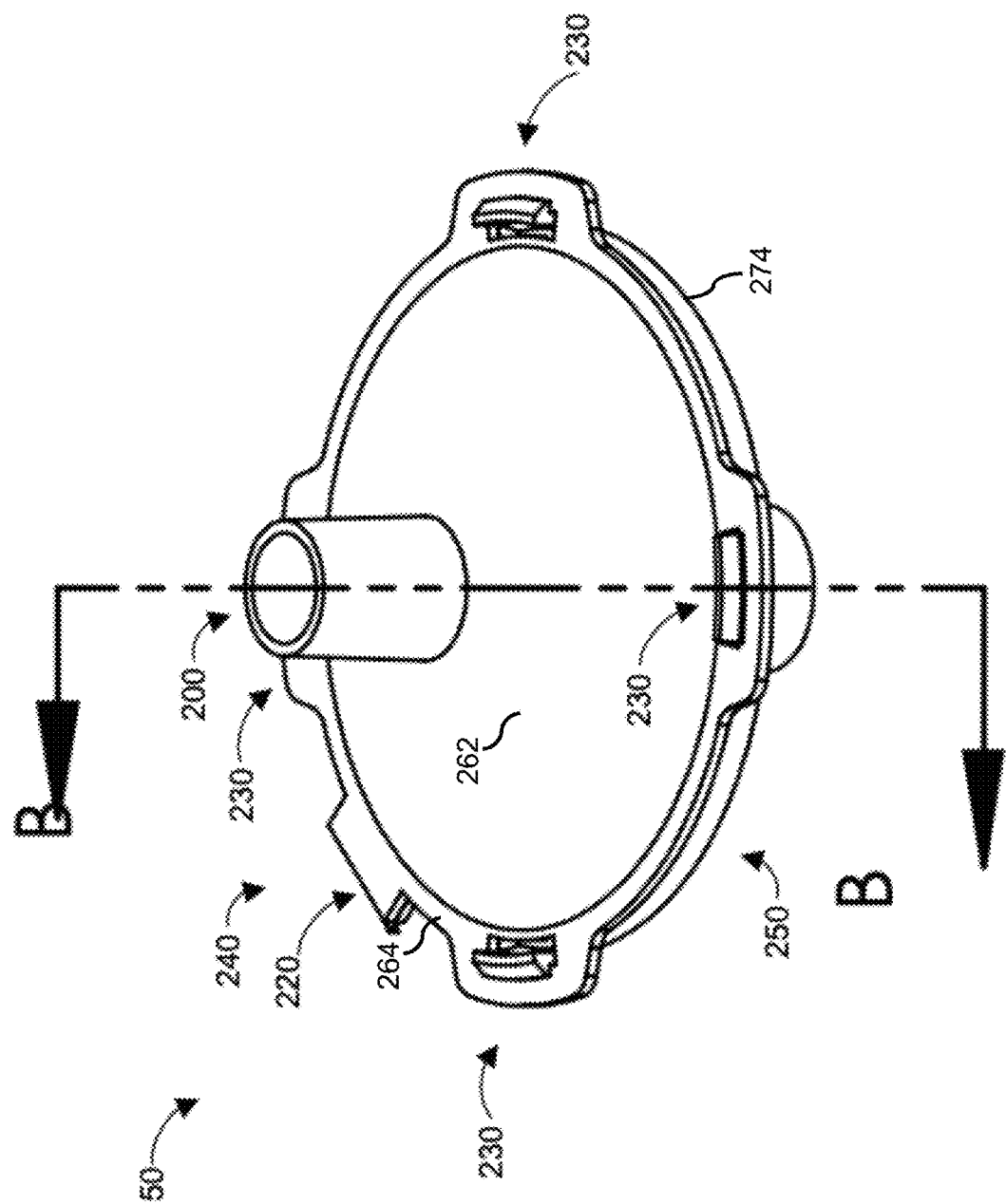
FIG. 5 is a perspective view of a gas filter housing in a closed state according to another embodiment.

FIG. 5 is a perspective view of a medical breathing gas filter housing 50 in a closed state according to another embodiment. Gas filter housing 50 is the same as or similar to gas filter housing 20 except that gas filter housing 50 includes a gasket or O-ring 500 (FIG. 6) to improve the gas seal between the top and bottom housing bodies 240, 250 of the gas filter housing 50. The O-ring 500 is disposed in a sealing channel 510 defined between the first outer ridge 244 and a sealing outer ridge 514. The sealing outer ridge 514 is attached to the top housing body 240. The sealing channel 510 is also defined by the interior side 253 of the bottom housing body 250. For example, the bottom housing body 250 includes an annular body 520 attached to the conical portion 272, and the annular body 520 partially defines the sealing channel 510.

Gas filter housing 50 includes 4 snap clips 230 while filter 20 includes 3 snap clips 230. However, either or both gas filter housings 20, 50 can include additional or fewer snap clips 230. In some embodiments, gas filter housings 20, 50 can have the same number of snap clips 230.

Figure 6:
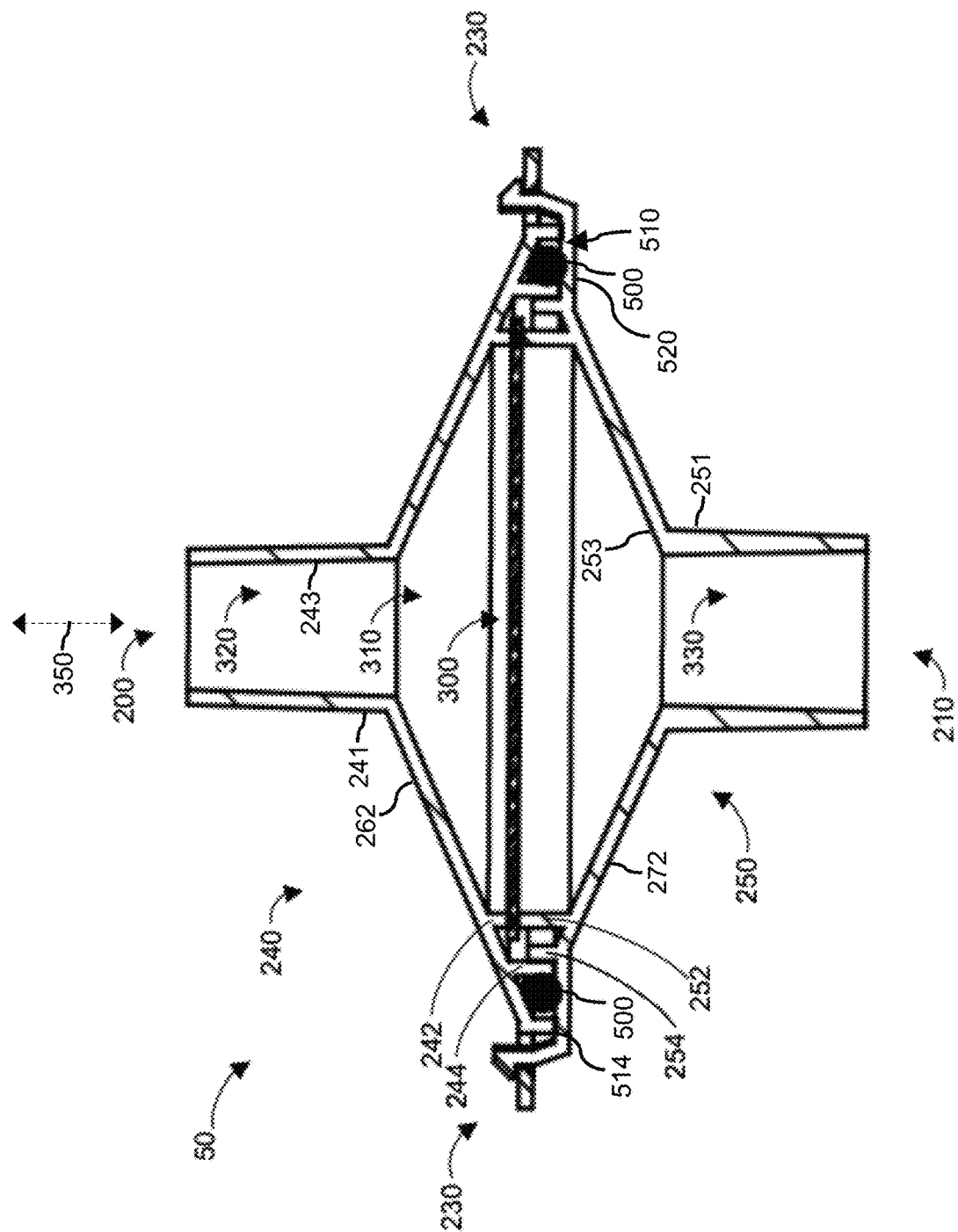
FIG. 6 is a cross-sectional view of the gas filter housing illustrated in FIG. 5.
Figure 7:
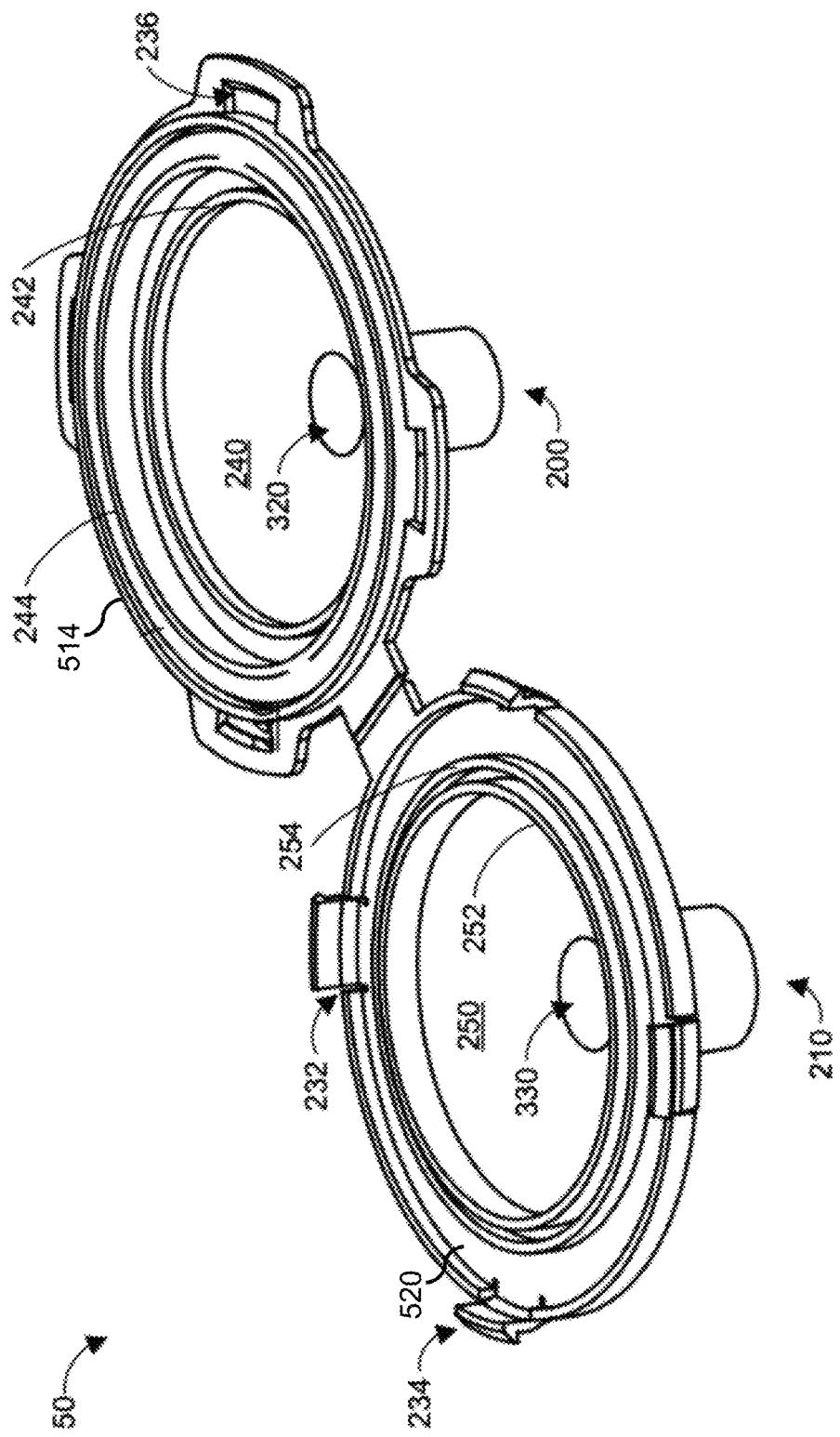
FIG. 7 is a perspective view of gas filter housing illustrated in FIG. 5 in an open state with the gas filter media and the O-ring removed.

FIG. 6 is a cross-sectional view of gas filter housing 50 through line B-B in FIG. 5. FIG. 7 is a perspective view of gas filter housing 50 in an open state with the gas filter media 300 and the O-ring 500 removed.

Figure 8:
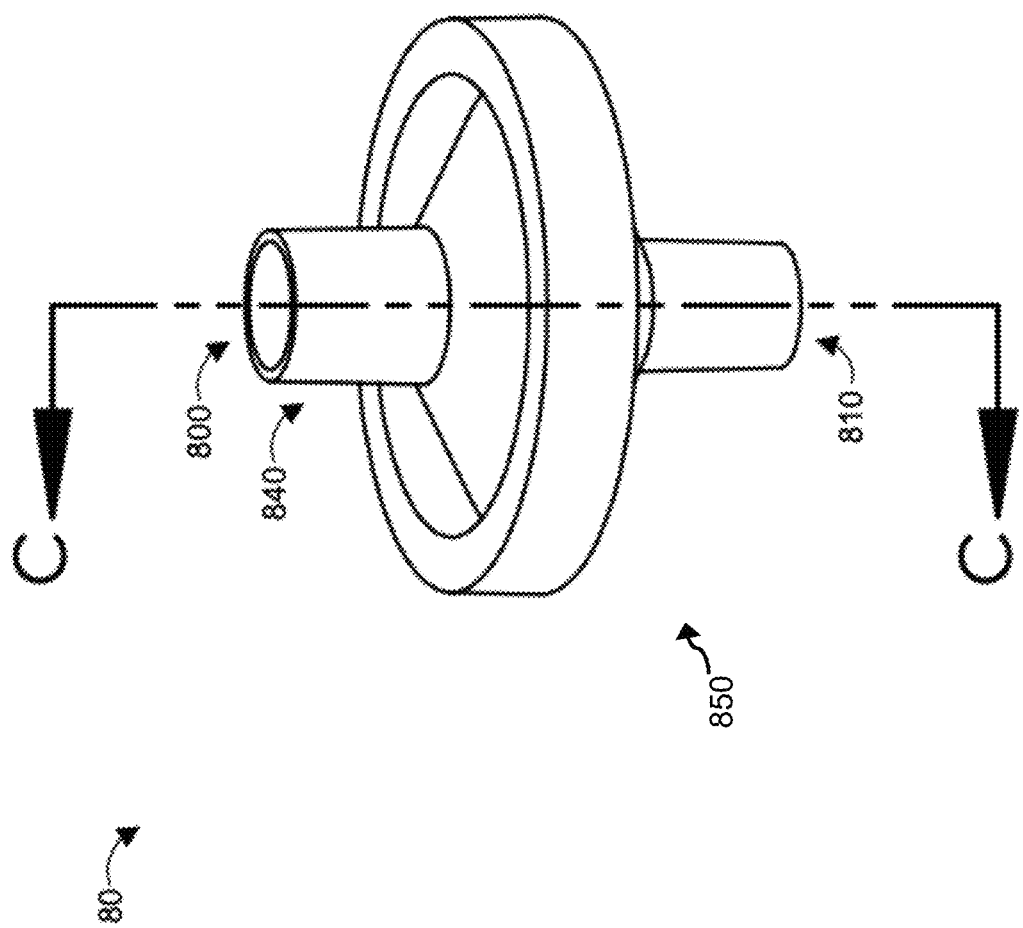
FIG. 8 is a perspective view of a gas filter housing in a closed state according to another embodiment.

FIG. 8 is a perspective view of a medical breathing gas filter housing 80 in a closed state according to another embodiment. The gas filter housing 80 includes ports 800, 810 that can be the same as or similar to ports 200, 210, respectively. The gas filter housing 80 also includes top and bottom housing bodies 840, 850, respectively, that are releasably rotatably connected by threads, which can provide a gas seal. The top and bottom housing bodies 840, 850 are symmetrical and/or complementary such that when the top and bottom housing bodies 840, 850 are rotatably secured together, a gas seal is formed. In some embodiments, a gasket such an O-ring can be disposed between the top and bottom housing bodies 840, 850 (e.g., at or between an interface between the top and bottom housing bodies 840, 850) to provide and/or improve the gas seal.

Figure 9:
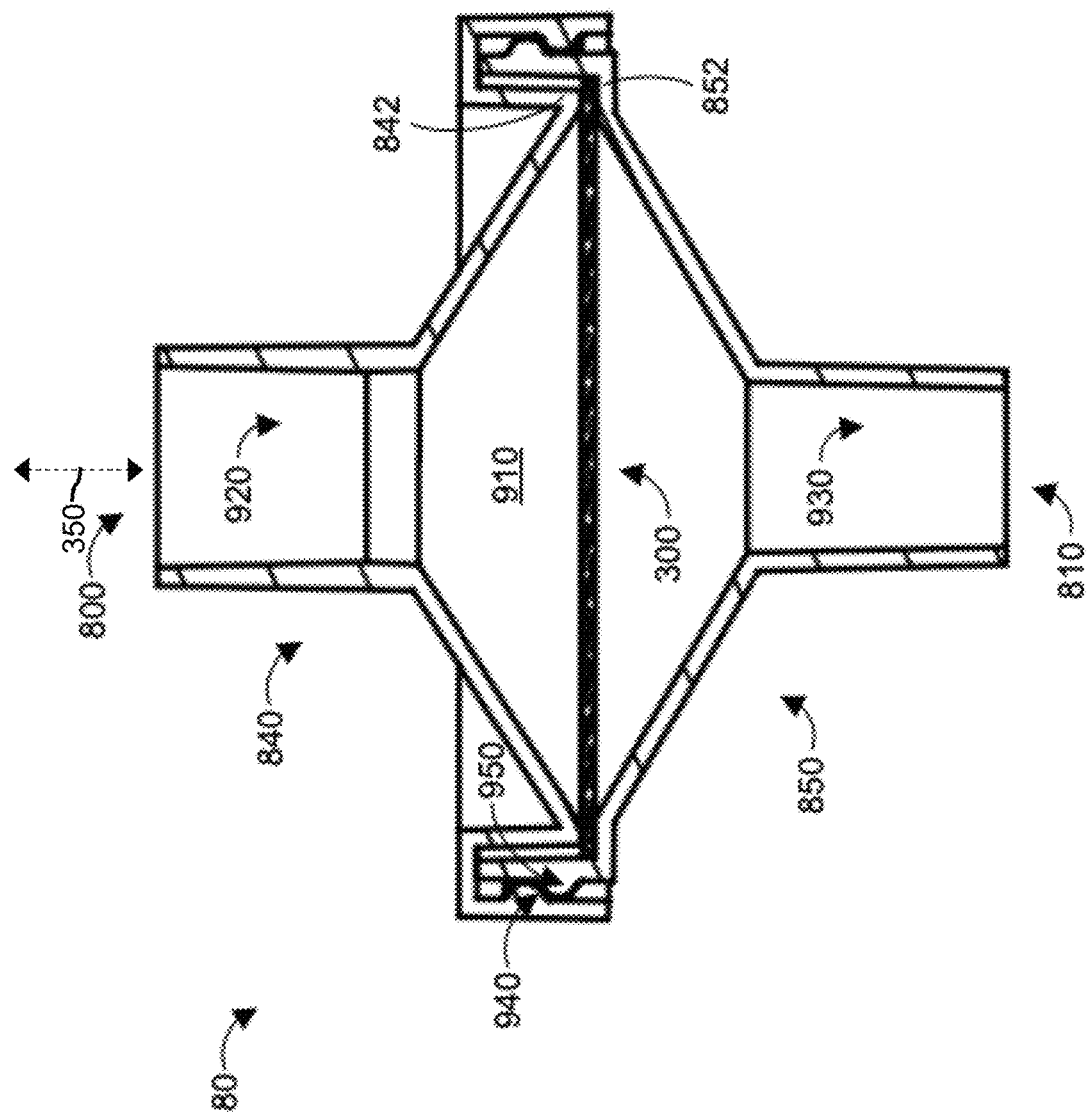
FIG. 9 is a cross-sectional view of the gas filter housing illustrated in FIG. 8.

FIG. 9 is a cross-sectional view of gas filter housing 90 through line C-C in FIG. 8. The cross-sectional view illustrates that the top and bottom housing bodies 840, 850 include complementary threaded surfaces 940, 950, respectively. A replaceable gas filter media 300 is disposed in a cavity 910 defined by the top and bottom housing bodies 840, 850 of the gas filter housing 80. A first channel 920 extends from the port 800 to the cavity 910. A second channel 930 extends from the cavity 910 to the port 810. When port 800 is an inlet port and port 810 is an outlet port, the first channel 920 is an inlet channel and the second channel 930 is an outlet channel. Conversely, when port 810 is the inlet port and port 800 is the outlet port, the first channel 920 is the outlet channel and the second channel 930 is the inlet channel.

The top housing body 840 includes a ridge 842 that is aligned with an opposing surface 852 on the bottom housing body 850 to grip and/or compress the gas filter media 300.

Figure 10:
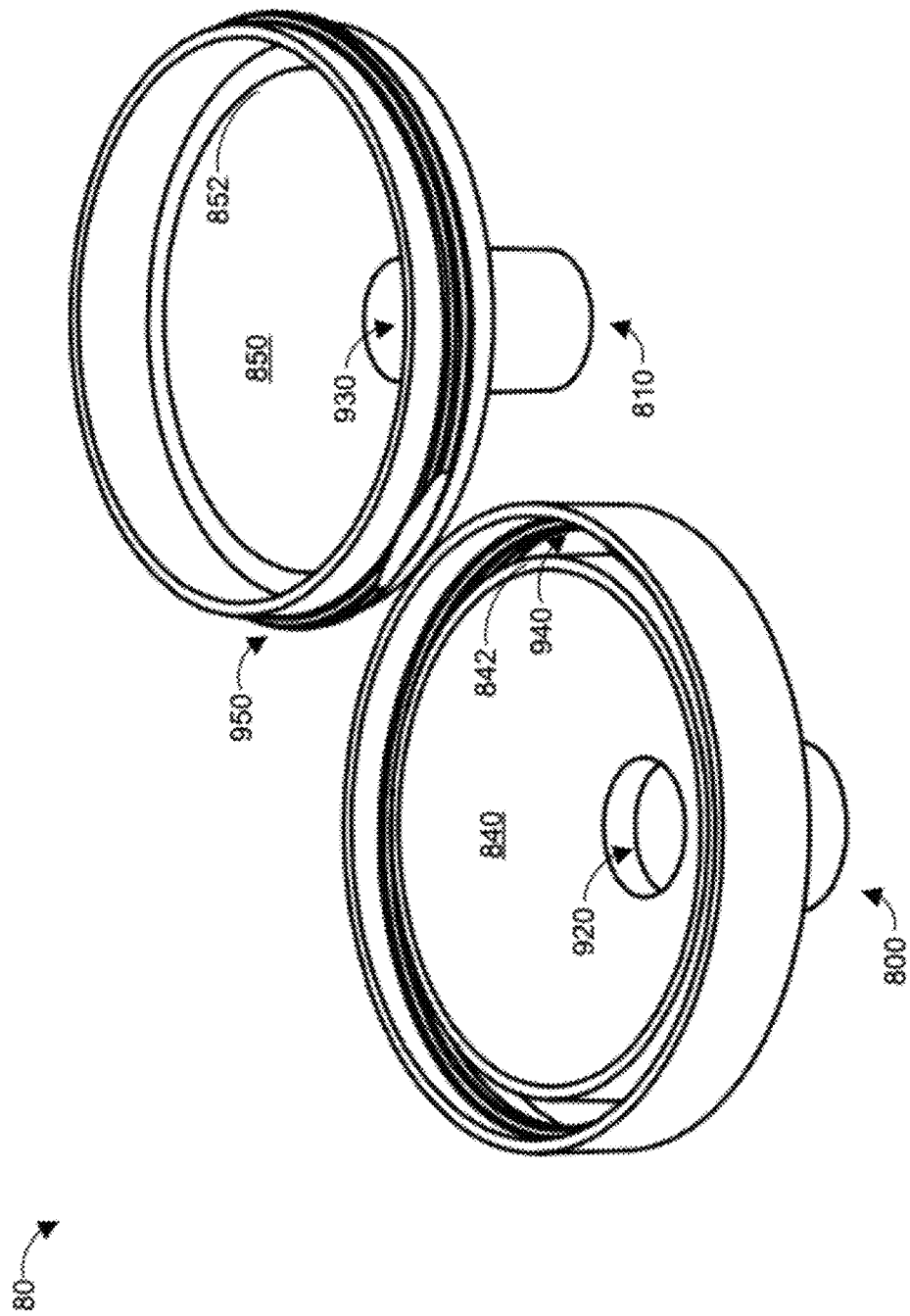
FIG. 10 is a perspective view of gas filter housing illustrated in FIG. 8 in an open state with the gas filter media removed.

FIG. 10 is a perspective view of gas filter housing 80 in an open state with the gas filter media 300 removed. As illustrated, threaded surface 940 is defined on an interior surface of the top housing body 840, and threaded surface 950 is defined on an exterior surface of the bottom housing body 850. Alternatively, gas filter housing 80 can be configured and arranged such that the threaded surface 940 is defined on an exterior surface of the top housing body 840, and threaded surface 950 is defined on an interior surface of the bottom housing body 850.

Figure 11:
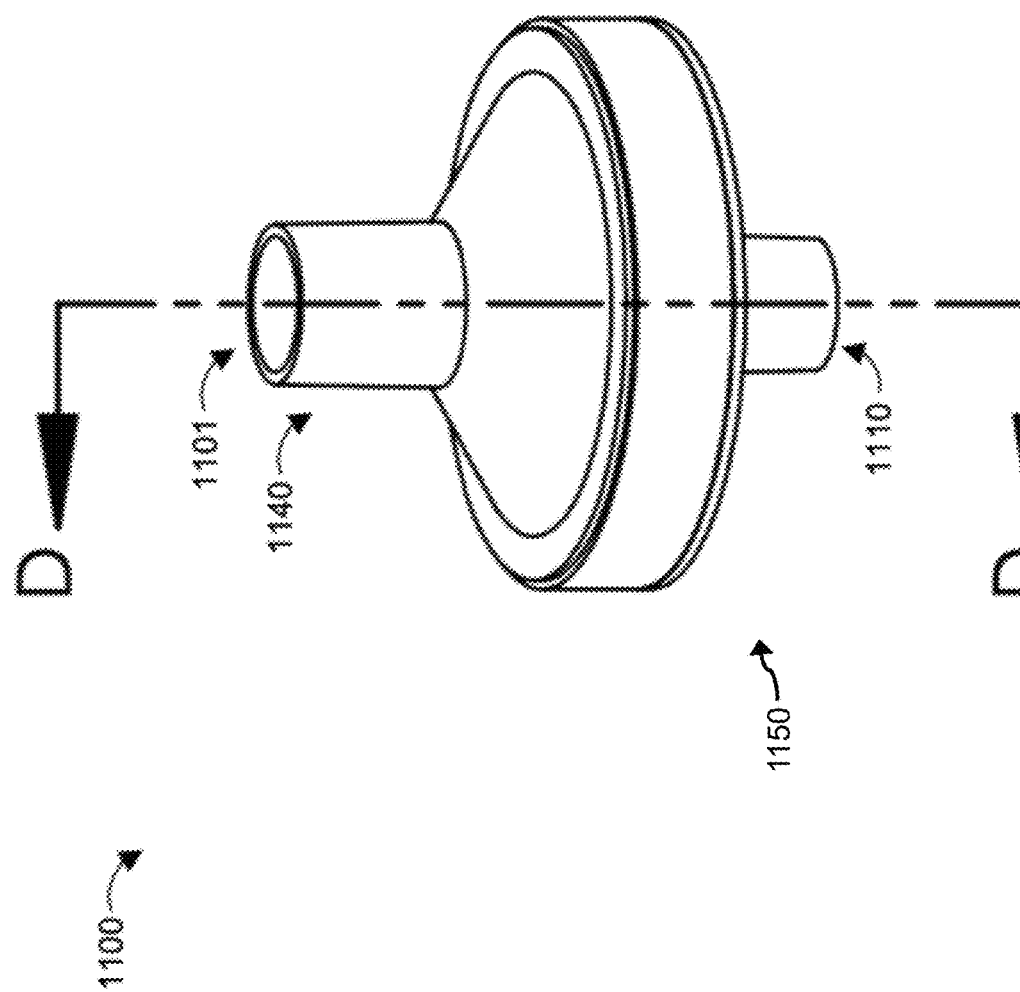
FIG. 11 is a perspective view of a gas filter housing in a closed state according to another embodiment.

FIG. 11 is a perspective view of a medical breathing gas filter housing 1100 in a closed state according to another embodiment. Gas filter housing 1100 is the same as gas filter housing 80 except that their relative geometries are different. The gas filter housing 1100 includes ports 1101, 1110 that can be the same as or similar to ports 800, 810, respectively. The gas filter housing 1100 also includes top and bottom housing bodies 1140, 1150, respectively, that are releasably rotatably connected by threads. The top and bottom housing bodies 1140, 1150 are symmetrical and/or complementary such that when the top and bottom housing bodies 1140, 1150 are rotatably secured together, a gas seal is formed. The top and bottom housing bodies 1140, 1150 can be the same as or similar to top and bottom housing bodies 840, 850, respectively In some embodiments, a gasket such an O-ring can be disposed between the top and bottom housing bodies 1140, 1150 (e.g., at or between an interface between the top and bottom housing bodies 1140, 1150) to provide and/or improve the gas seal.

Figure 12:
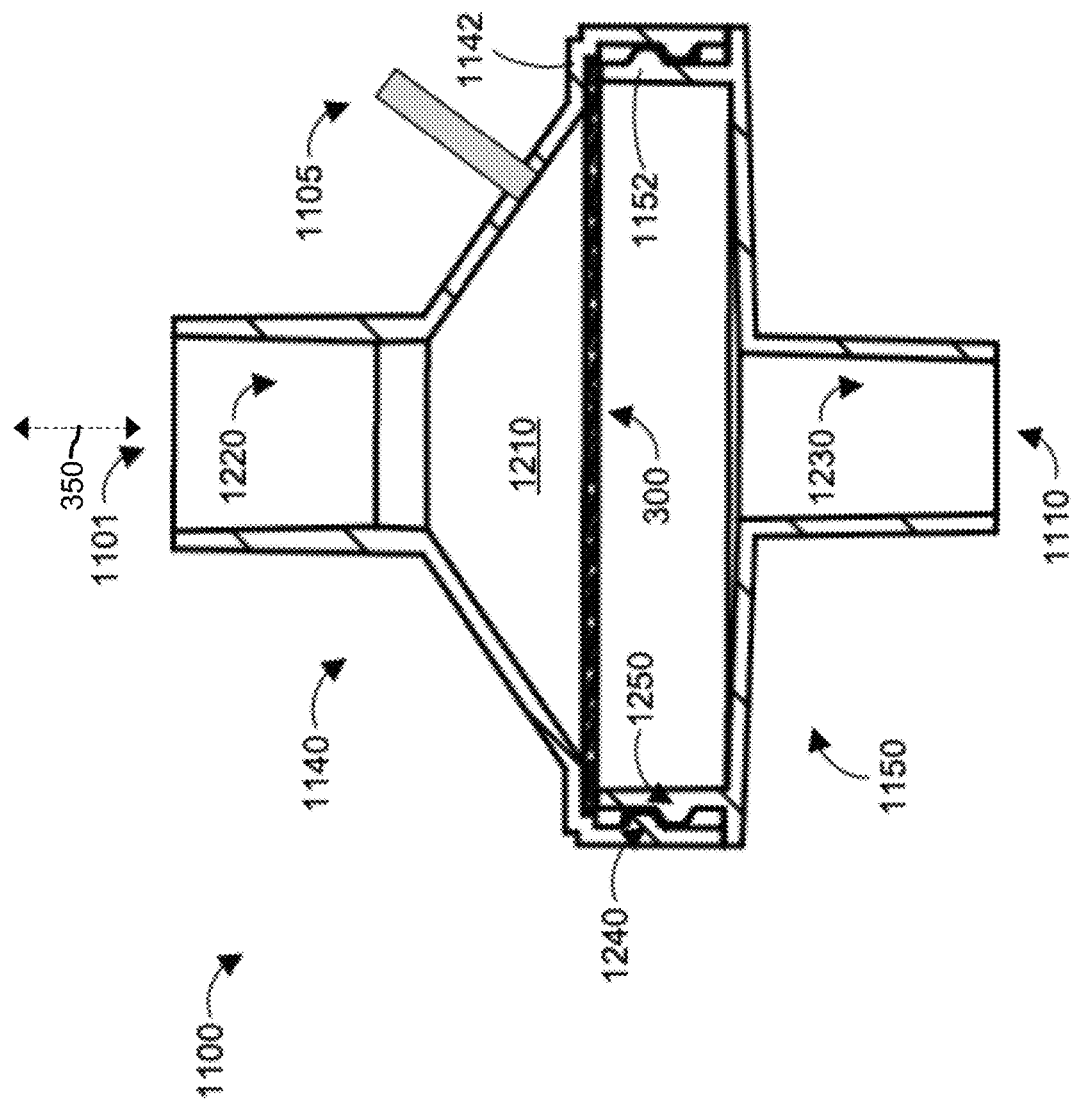
FIG. 12 is a cross-sectional view of the gas filter housing illustrated in FIG. 11.

FIG. 12 is a cross-sectional view of gas filter housing 1100 through line D-D in FIG. 11. The cross-sectional view illustrates that the top and bottom housing bodies 1140, 1150 include complementary threaded surfaces 1240, 1250, respectively, that are engaged in the closed state. A replaceable gas filter media 300 is disposed in a cavity 1210 defined by the top and bottom housing bodies 1140, 1150 of the gas filter housing 1100. A first channel 1220 extends from the port 1101 to the cavity 1210. A second channel 1230 extends from the cavity 1210 to the port 1110. When port 1101 is an inlet port and port 1110 is an outlet port, the first channel 1220 is an inlet channel and the second channel 1230 is an outlet channel. Conversely, when port 1110 is the inlet port and port 1101 is the outlet port, the first channel 1220 is the outlet channel and the second channel 1230 is the inlet channel.

The bottom housing body 1150 includes a ridge 1152 that is aligned with an opposing surface 1142 on the top housing body 1140 to grip and/or compress the gas filter media 300.

FIG. 12 also illustrates an optional gas sampling port 1105. Any of the gas filter housings described herein can include a gas sampling port that is the same as or different than gas sampling port 1105.

Figure 13:
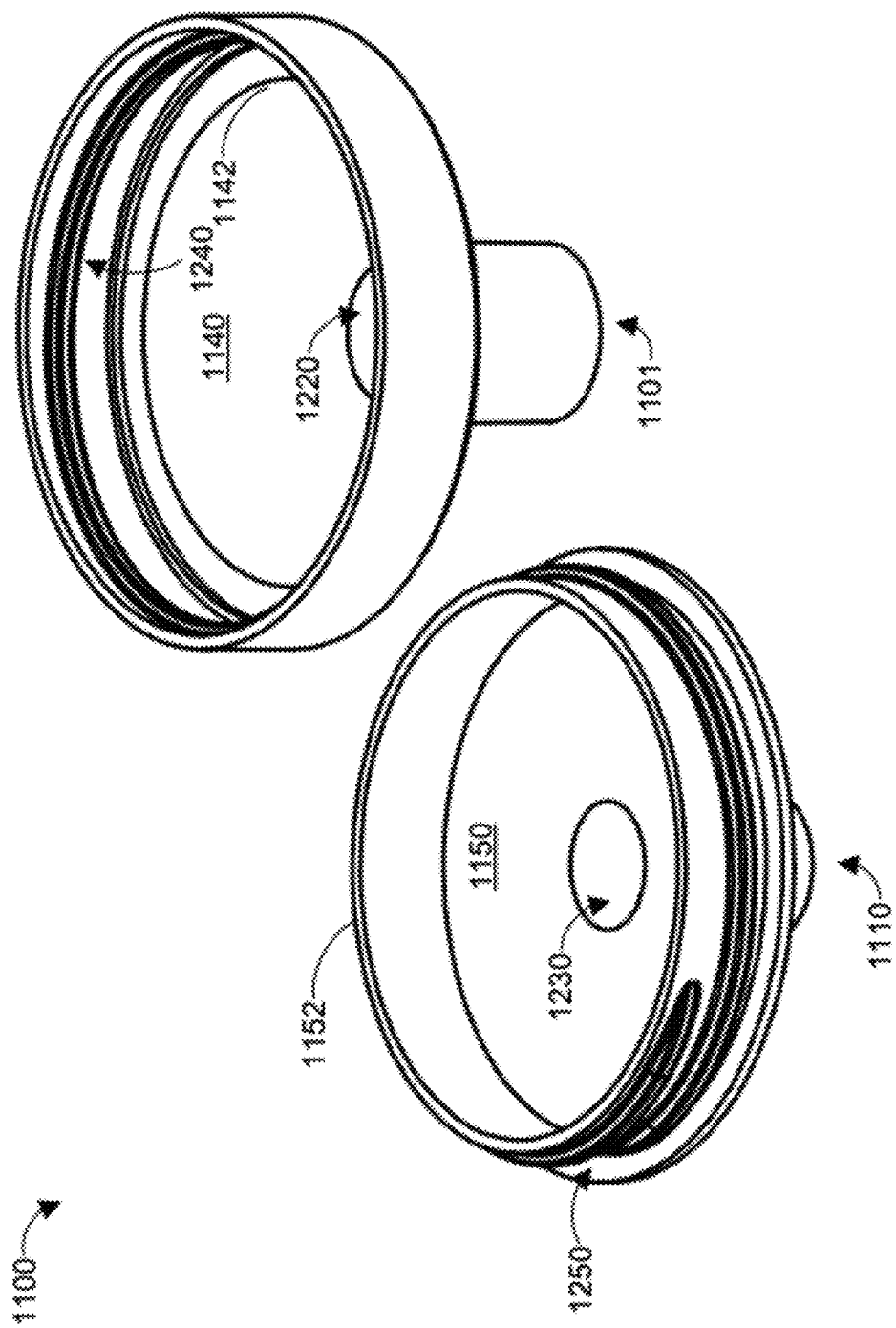
FIG. 13 is a perspective view of gas filter housing illustrated in FIG. 11 in an open state with the gas filter media removed.

FIG. 13 is a perspective view of gas filter housing 1100 in an open state with the gas filter media 300 removed. As illustrated, threaded surface 1240 is disposed on an interior surface of the top housing body 1140, and threaded surface 1250 can be disposed on an exterior surface of the bottom housing body 1150. Alternatively, gas filter housing 1100 can be configured and arranged such that the threaded surface 1240 is disposed on an exterior surface of the top housing body 1140, and threaded surface 1250 is disposed on an interior surface of the bottom housing body 1150. The complementary threaded surfaces 1240, 1250 are disengaged in the open state.

Figure 14:
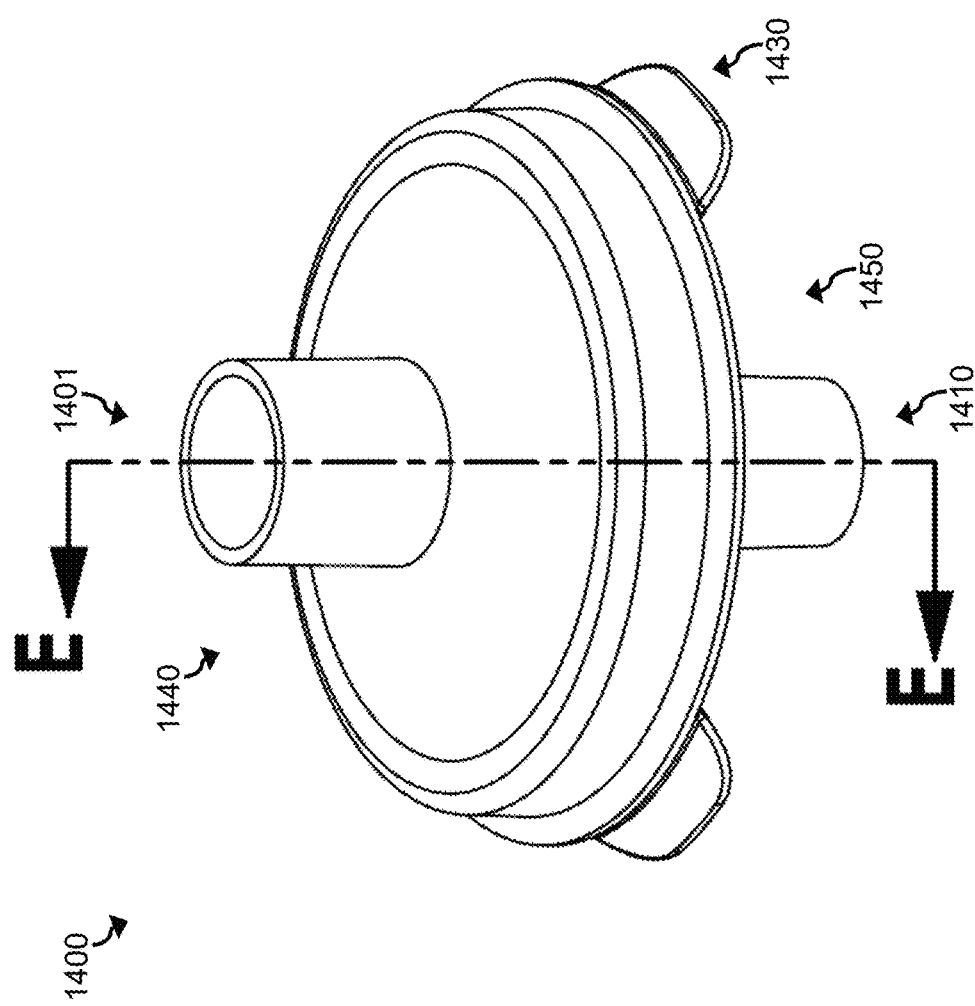
FIG. 14 is a perspective view of a gas filter housing in a closed state according to another embodiment.

FIG. 14 is a perspective view of a medical breathing gas filter housing 1400 in a closed state according to another embodiment. The gas filter housing 1400 includes ports 1401, 1410 that can be the same as or similar to ports 200, 210, respectively. The gas filter housing 1400 also includes top and bottom housing bodies 1440, 1450, respectively, that are detachably coupled. The top and bottom housing bodies 1440, 1450 are symmetrical and/or complementary such that when the top and bottom housing bodies 1440, 1450 are attached and/or secured together, a gas seal is formed.

In the closed state, the top and bottom housing bodies 1440, 1450 are releasably secured (e.g., snap fit) by snap clips 1430 that are attached to the top housing body 1440 and that are releasably secured to the bottom housing body 1450. In another embodiment, the snap clips 1430 can be attached to the bottom housing body 1450 and releasably secured to the top housing body 1440.

Figure 15:
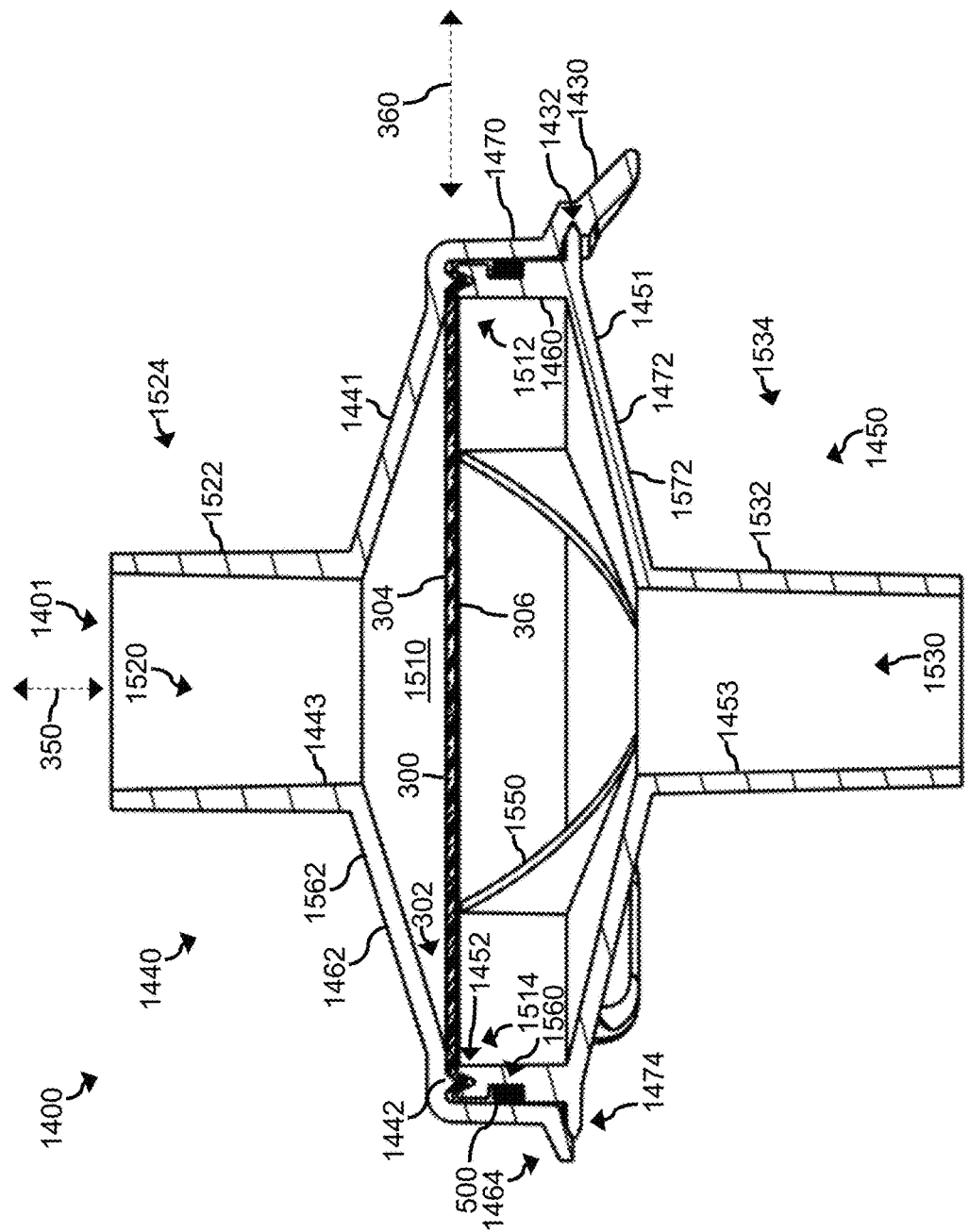
FIG. 15 is a cross-sectional view of the gas filter housing illustrated in FIG. 14.

FIG. 15 is a cross-sectional view of gas filter housing 1400 through line E-E in FIG. 14. As illustrated, the top housing body 1440 includes a conical portion 1462 and a flange 1464. The conical portion 1462 is disposed between and/or is attached to the first port 1401 and the flange 1464. The bottom housing body 1450 includes a conical portion 1472 and a flange 1474. The conical portion 1472 is disposed between and/or is attached to the second port 1410 and the flange 1474. The top and bottom housing bodies 1440, 1450 have a respective exterior side 1441, 1451 and a respective interior side 1443, 1453.

The conical portions 1462, 1472 are formed by walls 1562, 1572, and the walls 1562, 1572 define a cavity 1510. The cavity 1510 is configured and/or sized to receive a replaceable gas filter media 300 such that the replaceable gas filter media 300 extends from a first end 1512 to a second end 1514 of the cavity 1510.

A first channel 1520 extends between and fluidly couples the first port 1401 and the cavity 1510. A second channel 1530 extends between and fluidly couples the second port 1410 and the cavity 1510. The ports 1401, 1410 are aligned along a vertical axis of symmetry 350 through the gas filter housing 1400. The vertical axis of symmetry 350 is orthogonal to the top and bottom surfaces 304, 306 of the replaceable gas filter media 300. The first and second channels 1520, 1530 are defined by walls 1522, 1532, respectively. The walls 1522, 1532 form tubular portions 1524, 1534, respectively.

The conical portions 1462, 1472 are oriented in opposing directions to form a complementary structure in which the top conical portion 1462 is disposed on the bottom conical portion 1472. The portion of the top conical portion 1462 near the first channel 1520 has a narrower cross-sectional width than the portion of the top conical portion 1462 near the replaceable gas filter media 300. In addition, the portion of the bottom conical portion 1472 near the second channel 1530 has a narrower cross-sectional width than the portion of the bottom conical portion 1472 near the replaceable gas filter media 300. The cross-sectional width of the conical portions 1462, 1472 can be measured with respect to the horizontal axis 360.

The top conical portion 1462 includes an inner ridge 1442 that is aligned with an inner slot or indentation 1452 defined in the bottom conical portion 1452. For example, the inner ridge 1442 and the inner slot 1452 are disposed at the same radius from the vertical axis of symmetry 350. The inner ridge 1442 and inner slot 1452 are configured to grip, compress, and/or engage the top side 304 of the replaceable gas filter media 300 along its sides or edges 302 when the gas filter housing 1400 is in the closed state. The inner ridge 1442 and the inner slot 1452 can extend in a circle or ring along conical portions 1462, 1472, respectively, defined by their respective radii. The inner slot 1452 is defined in a vertical wall 1460 that is attached to an outer edge of the bottom conical portion 1472. The vertical wall 1460 extends towards the outer edge of the top conical portion 1462 and parallel to the vertical axis of symmetry 350.

The flanges 1464, 1474 are aligned and configured to be in direct physical contact with each other when the gas filter housing 1400 is in the closed state. A vertical wall 1470 is attached to an outer edge of the top conical portion 1462. The vertical walls 1460, 1470 are horizontally (e.g., radially) offset from each other and in direct physical contact with each other. For example, the vertical walls 1460, 1470 are disposed at the different radii from the vertical axis of symmetry 350. The vertical walls 1460, 1470 and the flanges 1464, 1474 can provide a gas seal when the gas filter housing 1400 is in the closed state.

An optional O-ring 500 is disposed in a slot 1560 defined in the outer surface of the vertical wall 1460 to provide and/or improve the gas seal. The O-ring 500 is disposed at an interface between the top and bottom housing bodies 1440, 1450 (e.g., between vertical walls 1460, 1470).

A plurality of ribs 1550 are optionally disposed on the interior side 1453 of the bottom housing body 1450. The ribs 1550 can comprise a wall or other structure. The ribs 1550 can provide an orientation of the gas filter housing 1400, can improve the strength and/or rigidity of the gas filter housing 1400, and/or can prevent the user from putting the replaceable gas filter media 300 on the wrong side of the cavity 1510.

The snap clips 1430 have a notch or slot 1432 defined on an interior side of the snap clips 1430. The notch or slot 1432 forms a hook that can releasably engage the flange 1474 to releasably attach (e.g., snap fit) the top and bottom housing bodies 1440, 1450. The snap clips 1430 can comprise a lever in some embodiments.

Figure 16:
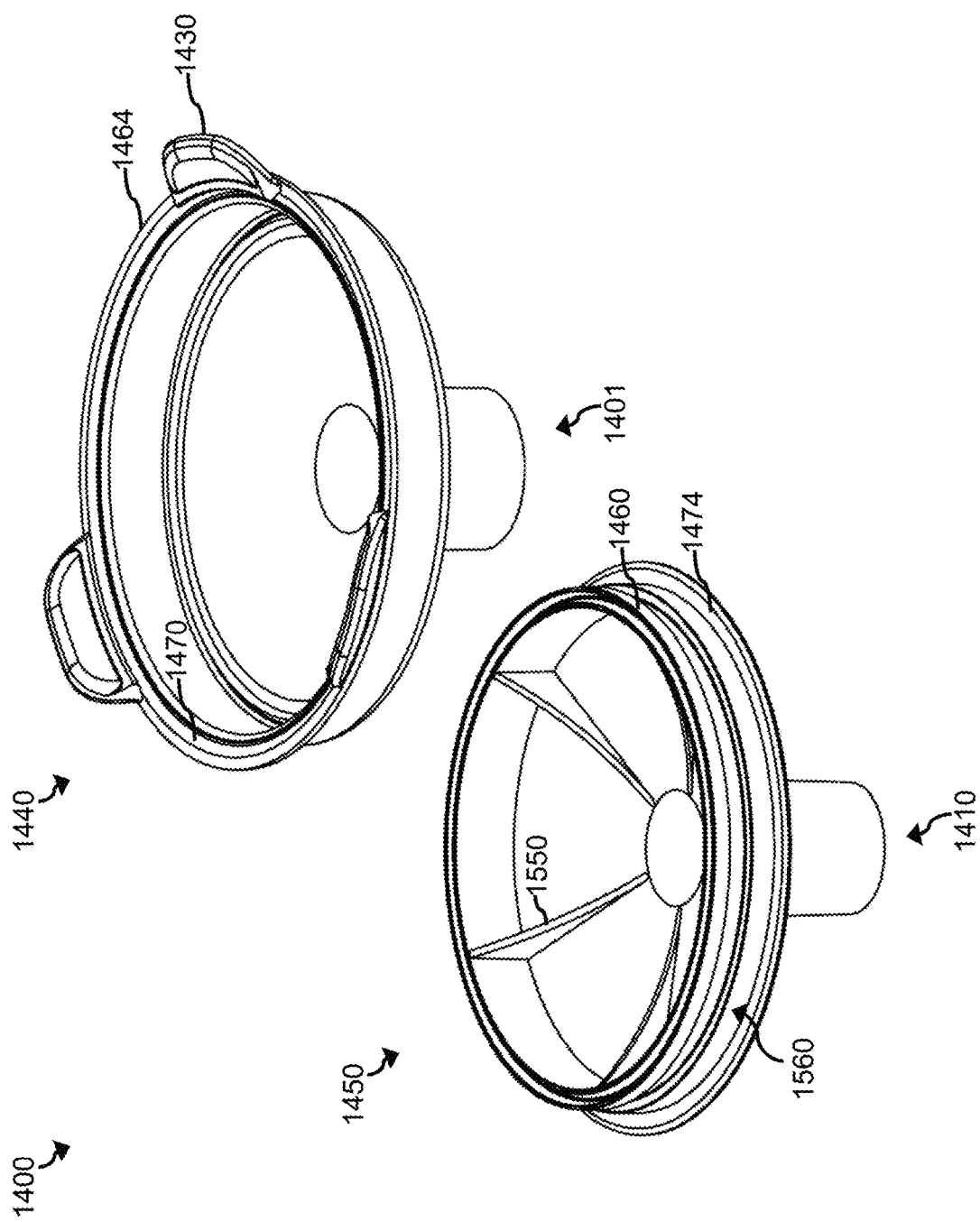
FIG. 16 is a perspective view of gas filter housing illustrated in FIG. 14 in an open state with the gas filter media and the O-ring removed.

FIG. 16 is a perspective view of gas filter housing 50 in an open state with the gas filter media 300 and the O-ring 500 removed.

The gas filter housings described herein can comprise a medical grade rigid plastic such as polyethylene, polypropylene, polymethyl methacrylate (PMMA), polyvinyl chloride (PVC), polyamide, acrylonitrile butadiene styrene (ABS), and/or polycarbonate. These examples are not limiting and are only provided as illustrative embodiments. Those skilled in the art will appreciate any equivalent or alternative material compositions, which are similar comprehended by this disclosure and invention.

Though the replaceable gas filter media and gas filter housings are described with respect to bCPAP and CPAP systems, the replaceable gas filter media and gas filter housings can be used in other medical respiratory systems such as mechanical ventilator systems.

In some embodiments, one or more features and/or structures in gas filter housings 20, 50, 80, 1100, and/or 1400 can be combined.

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

What is claimed is:

1. A medical breathing gas filter housing comprising:
a first housing body comprising a first conical body, a first tubular body, and a first flange, the first conical body tapering from a first end to a second end, the first tubular body attached to the second end of the first conical body to form a first port, the first flange disposed at the first end of the first conical body;
a second housing body comprising a second conical body, a second tubular body, and a second flange, the second conical body tapering from a first end to a second end, the second tubular body attached to the second end of the second conical body to form a second port, the second flange coupled to the second end of the second conical body; and
a plurality of snap clips, each snap clip comprising:
a rigid projection having opposing planar surfaces, the rigid projection extending from the first flange;
a hook attached to an end of the rigid projection; and
a slot defined in the second flange, the slot configured to removably receive the hook and the rigid projection;
wherein:
the gas filter housing is configurable between a closed state and an open state,
in the closed state:
the first flange is disposed on the second flange such that first and second interior sides of the first and second housing bodies, respectively, define a cavity, the cavity sized to receive a replaceable gas filter media, and
in each snap clip, the hook and the rigid projection are inserted through the slot and the hook engages the second flange to secure the snap clip, and
in the open state:
in each snap clip, the hook is disengaged from the second flange and the hook and the rigid projection are removed from the slot, and
the first flange is spaced apart from the second flange to provide access to the replaceable gas filter media.

2. The filter housing of claim 1, wherein:
a first ridge extends from the first interior side of the first housing body,
a second ridge extends from the second interior side of the second housing body, and
when the gas filter housing is in the closed state, the first and second ridges engage top and bottom sides, respectively of the replaceable gas filter media.

3. The filter housing of claim 2, wherein the first and second ridges are aligned when the gas filter housing is in the closed state.

4. The filter housing of claim 2, wherein:
the first and second ridges are first and second inner ridges, respectively,
an outer ridge extends from the first interior side of the first housing body,
a groove is defined in the second interior side of the second housing body, and
when the gas filter housing is in the closed state, the outer ridge is disposed in the groove.

5. The filter housing of claim 4, wherein when the gas filter housing is in the closed state, the outer ridge and the groove form a seal.

6. The filter housing of claim 5, wherein:
the outer ridge is a first outer ridge,
a second outer ridge extends from the second interior side of the second housing body, and
the groove is defined between the second outer ridge and the second flange.

7. The filter housing of claim 6, wherein:
a sealing outer ridge extends from the first interior side of the first housing body,
a sealing channel is defined between the sealing outer ridge and the first outer ridge, and
a gasket is disposed in the sealing channel.

8. The filter housing of claim 7, wherein the gasket comprises an O-ring.

9. The filter housing of claim 7, wherein the second housing body further comprises an annular body, the annular body disposed between the second conical body and the second flange, the annular body further defining the sealing channel.

10. The filter housing of claim 1, further comprising a hinge attached to the first and second housing bodies.

11. The filter housing of claim 1, wherein the first and second ports are aligned along an axis of symmetry of the filter housing.

12. A medical breathing gas filter housing comprising:
a first housing body comprising a first conical body, a first tubular body, and a first flange, the first conical body tapering from a first end to a second end, the first tubular body attached to the second end of the first conical body to form a first port, the first flange disposed at the first end of the first conical body;
a second housing body comprising a second conical body, a second tubular body, an annular body, and a second flange, the second conical body tapering from a first end to a second end, the second tubular body attached to the second end of the second conical body to form a second port, the annular body disposed between the second conical body and the second flange; and
a plurality of snap clips, each snap clip comprising:
a rigid projection having opposing planar surfaces, the rigid projection extending from the first flange;
a hook attached to an end of the rigid projection; and
a slot defined in the second flange, the slot configured to removably receive the hook and the rigid projection;
wherein:
the gas filter housing is configurable between a closed state and an open state, a plurality of ridges, including first and second ridges, are attached to a first interior side of the first conical body, in the closed state:
the first flange is disposed on the second flange such that first and second interior sides of the first and second housing bodies, respectively, define a cavity, the cavity sized to receive a replaceable gas filter media, and
in each snap clip, the hook and the rigid projection are inserted through the slot and the hook engages the second flange to secure the snap clip, and in the open state:
the first flange is spaced apart from the second flange to provide access to the replaceable gas filter media, and
in each snap clip, the hook is disengaged from the second flange and the hook and the rigid projection are removed from the slot.

13. The filter housing of claim 12, wherein in the closed state the first and second ridges extend to the annular body.

14. The filter housing of claim 12, further comprising a gasket disposed in a sealing channel defined between the first and second ridges, the sealing channel further defined by the annular body.

15. The filter housing of claim 14, wherein the gasket comprises an O-ring.

16. The filter housing of claim 12, further comprising a sampling port disposed on the first exterior side of the first housing body, the sampling port fluidly coupled to the cavity when the gas filter housing is in the closed state.

17. The filter housing of claim 12, wherein the first and second ports are aligned along an axis of symmetry of the filter housing.

18. A medical breathing gas filter housing comprising:
a first housing body comprising a first conical body, a first tubular body, and a first flange, the first conical body tapering from a first end to a second end, the first tubular body attached to the second end of the first conical body to form a first port, the first flange disposed at the first end of the first conical body;
a second housing body comprising a second conical body, a second tubular body, an annular body, and a second flange, the second conical body tapering from a first end to a second end, the second tubular body attached to the second end of the second conical body to form a second port, the annular body disposed between the second conical body and the second flange; and
a plurality of snap clips, each snap clip comprising:
a rigid projection having opposing planar surfaces, the rigid projection extending from the second flange;
a hook attached to an end of the rigid projection; and
a slot defined in the first flange, the slot configured to removably receive the hook and the rigid projection;

wherein:
the gas filter housing is configurable between a closed state and an open state,
a plurality of ridges, including first and second ridges, are attached to a first interior side of the first conical body,
in the closed state:
the first flange is disposed on the second flange such that first and second interior sides of the first and second housing bodies, respectively, define a cavity, the cavity sized to receive a replaceable gas filter media, and
in each snap clip, the hook and the rigid projection are inserted through the slot and the hook engages the first flange to secure the snap clip, and
in the open state:
the first flange is spaced apart from the second flange to provide access to the replaceable gas filter media, and
in each snap clip, the hook is disengaged from the first flange and the hook and the rigid projection are removed from the slot.

19. The filter housing of claim 18, wherein in the closed state the first and second ridges extend to the annular body.

20. The filter housing of claim 18, further comprising a gasket disposed in a sealing channel defined between the first and second ridges, the sealing channel further defined by the annular body.

21. The filter housing of claim 20, wherein the gasket comprises an O-ring.

22. The filter housing of claim 18, further comprising a sampling port disposed on the first exterior side of the first housing body, the sampling port fluidly coupled to the cavity when the gas filter housing is in the closed state.

23. The filter housing of claim 18, wherein the first and second ports are aligned along an axis of symmetry of the filter housing.

* * * * *